United States Patent [19]

Shiba et al.

[11] Patent Number: 4,836,210
[45] Date of Patent: Jun. 6, 1989

[54] ULTRASONIC ANALYZER

[75] Inventors: Akira Shiba; Isamu Yamada; Keiichi Murakami, all of Kawasaki, Japan

[73] Assignee: Fujitsu Limited, Kawasaki, Japan

[21] Appl. No.: 204,908

[22] Filed: Jun. 10, 1988

[30] Foreign Application Priority Data

Jun. 15, 1987 [JP] Japan ............................ 62-148406
Jun. 15, 1987 [JP] Japan ............................ 62-148407
Jun. 19, 1987 [JP] Japan ............................ 62-152923

[51] Int. Cl.$^4$ ............................................. A61B 10/00
[52] U.S. Cl. ............................................. 128/660.06
[58] Field of Search ......................... 128/660.06; 73/599–600, 602

[56] References Cited

U.S. PATENT DOCUMENTS

4,389,893 6/1983 Ophir et al. ............... 128/660.06 X
4,569,353 2/1986 Ferrari ........................ 128/660.06
4,655,084 4/1987 Renzel ........................... 73/599 X

*Primary Examiner*—Francis Jaworski
*Attorney, Agent, or Firm*—Staas & Halsey

[57] ABSTRACT

An ultrasonic analyzer used in an ultrasonic diagnosis instrument for minimizing the effects of noise in echo signals. The analyzer includes: a first unit for determining a start point and an end point at an analysis interval to be analyzed based on an analysis selection signal and a time signal for an input time-series signal reflected from a media; second units for generating four kinds of integration values based on four kinds of multiplication signals, each of the multiplication signals being calculated by multiplying the analysis selection signal by the time signal, or a square signal of the time signal, or a product signal of the time signal and the time-series signal, or by the time-series signal or by the time-series signal; third units for storing each of the integration values by using the time signal as an address for storing; and a fourth unit for calculating a slope of a regression curve based on difference between the integration values, a determination of the differences being based on the stage point and the end point at the analysis interval.

17 Claims, 9 Drawing Sheets

Fig. 1A
PRIOR ART
ANALYSIS METHOD OF ECHO SIGNAL

Fig. 1B
ECHO SIGNAL

Fig. 1C
ANALYSIS SELECTION SIGNAL

Fig. 1D
PRIOR ART
ANALYSIS METHOD OF ECHO SIGNAL

Fig. 2

Fig. 3A TIME-SERIES SIGNAL y(t)

Fig. 3B ANALYSIS SELECTION SIGNAL w(t)

ULTRASONIC ANALYZER

BACKGROUND OF THE INVENTION

1. Field of the Invention

The present invention relates to an ultrasonic analyzer typically utilized for the diagnosis of a media, for example, a living body, in the field of medical instruments.

2. Description of the Related Art

An ultrasonic diagnosis instrument is widely utilized in the field of a medicine. This instrument irradiates ultrasonic pulses to the media, receives pulses reflected therefrom, and measures an acoustic characteristic, for example, an attenuation coefficient, of the reflected pulses (echo signals). The ultrasonic analyzer is used for analyzing the acoustic characteristic of echo signals received as time-series signals. In general, the echo signals contain much pulse noises which are not necessary for measuring the acoustic characteristic. These noises are caused by pulses reflected from various complex obstacles in the media, for example, complex blood vessels in the living body. Therefore, it is necessary to eliminate or avoid these noises to obtain a precise detection result when measuring the acoustic characteristic.

SUMMARY OF THE INVENTION

The object of the present invention is to provide an ultrasonic analyzer typically used in an ultrasonic diagnosis instrument and enabling high precision measurement of an acoustic characteristic of an echo signal reflected from a media.

In accordance with the present invention, there is provided a ultrasonic analyzer used in an ultrasonic diagnosis instrument including: a first unit for determining a start point and an end point at an analysis interval to be analyzed based on an analysis selection signal and a time signal for an input time-series signal reflected from a media; second units for generating four kinds of integration values based on four kinds of multiplication signals, each of the multiplication signals being calculated by multiplying the analysis selection signal by the time signal, or by a square signal of the time signal, or by an product signal of the time signal and the time-series signal, or by the time-series signal respectively; third units for storing each of the integration values by using the time signal as an address for storing; and a fourth unit for calculating a slope of a regression curve based on difference between the integration values, the determination of these differences being based on the start point and the end point of the analysis interval.

DESCRIPTION OF THE PREFERRED EMBODIMENTS

Before describing the preferred embodiments, an explanation will be given of a conventional method for analyzing an acoustic characteristic of an echo signal.

Figure 1A:
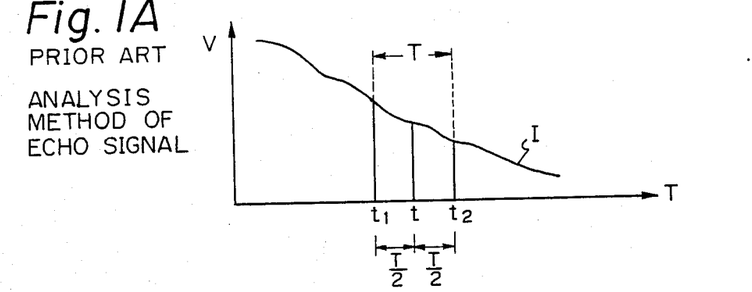
FIGS. 1A and 1D show a conventional method of analysis of an echo signal.
Figure 1B:
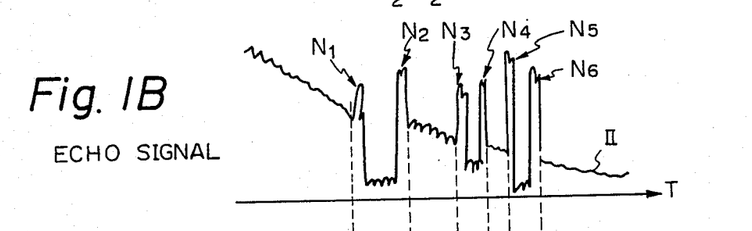
FIG. 1B is an actual waveform of an echo signal reflected from a media.
Figure 1C:
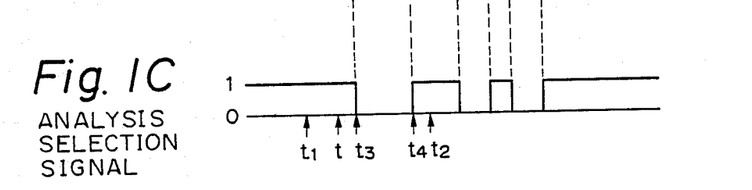
FIG. 1C is a waveform of an analysis selection signal.
Figure 1D:
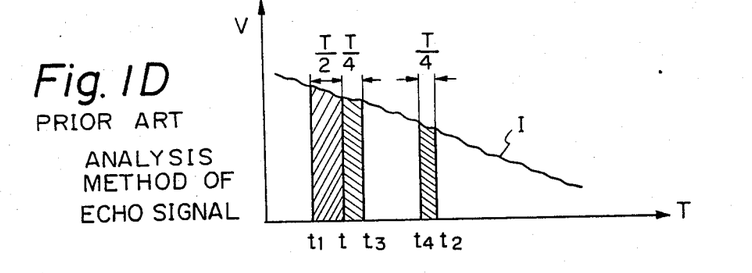

One example of the conventional method is shown in FIGS. 1A and 1D. In FIG. 1A, the curve I shows the input signal, i.e., the echo signal reflected from a living body. This curve is obtained by an envelope of the echo signal after passing through a logarithm amplifier (not shown). In the Figure, the ordinate V is the signal level of the input signal and the abscissa T is the transition time of the input signal. Therefore, the input signal can be described by a time-series signal and is analyzed within the analysis interval T. Each analysis interval has the same length. The time t is the central time of the analysis interval; the time $t_1$ is a start point of the analysis interval, and the time $t_2$ is an end point thereof. The intervals $t-t_1$ and $t_2-t$ are one half of the time of the analysis interval. The ultrasonic analyzer calculates a running average value for each analysis interval T and outputs the resultant data as a function of time. When pulse noise does not exist on the curve I, it is easy to obtain the start point $t_1$ and the end point $t_2$, since the analysis interval is constant. But, when pulse noises appear on the curve I, it is necessary to eliminate or avoid such noise intervals from the analysis interval in order to precisely detect the resultant data.

In FIG. 1B, the curve II shows an actual waveform of an input signal (echo signal) containing various pulse noises $N_1$ to $N_6$. These pulse noises appear when the irradiation pulses are reflected from various obstacles, for example, a blood vessel in the living body. Such noises also appear in the form of time-series signals.

In FIG. 1C, an analysis selection signal is used to eliminate the noise intervals. When the analysis selection signal is high level ("1"), an analysis is made of the analysis interval T. When the analysis selection signal is low level ("0"), the analysis is not made. In this case, assuming that the analysis is performed regardless of the high/low level of the analysis selection signal, it is impossible to precisely detect the result, since the resultant data contains noise components.

In FIG. 1D, the analysis interval is changed in such a way that the number of sampling data becomes constant in each analysis interval. That is, the number of sampling data of the analysis interval $t-t_1$ is equal to a sum of the intervals $t_3-t$ and $t_2-t_4$. In this case, when the analysis selection signal is low, such an interval is not used for calculating the number of sampling data.

Nevertheless, many very complex calculations are necessary to obtain each analysis interval, and accordingly, much time is needed to obtain an acoustic characteristic of the living body. This delay reduces the speed of the diagnosis of the living body.

An ultrasonic analyzer according to the present invention will be explained in detail hereinafter.

Figure 2:
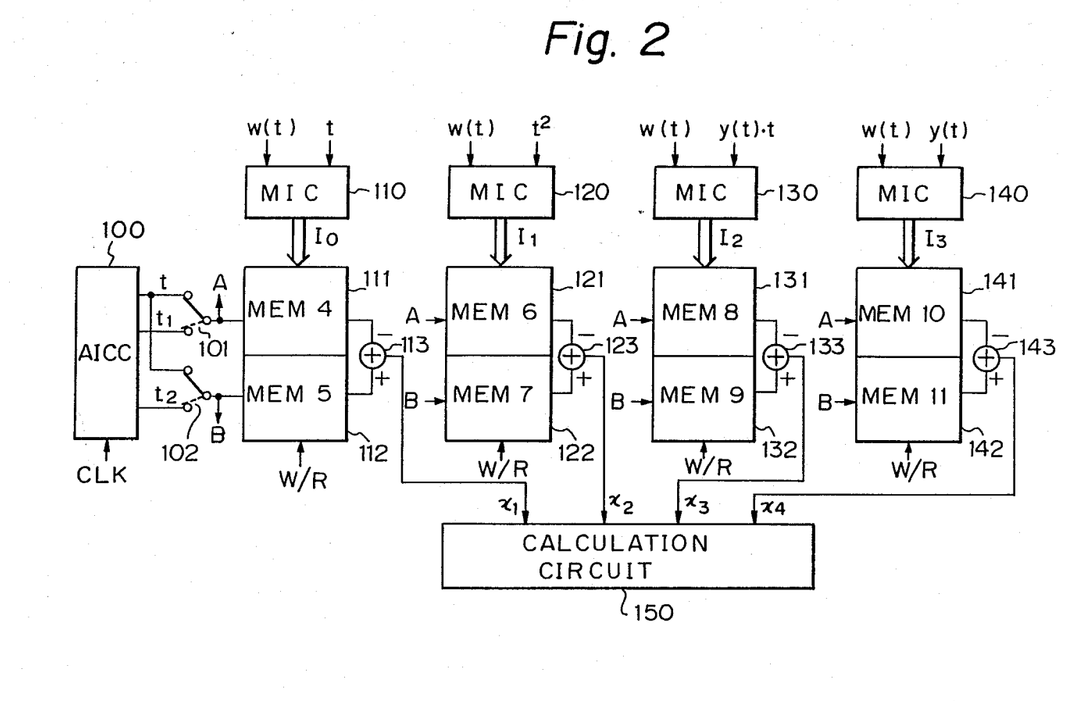
FIG. 2 is a schematic block diagram of an ultrasonic analyzer according to an embodiment of the present invention.

FIG. 2 is a schematic block diagram of the ultrasonic analyzer according to an embodiment of the present invention.

In FIG. 2, reference number 100 denotes an analysis interval calculation circuit (AICC), 110, 120, 130 and 140 are multiplication/integration circuits (MIC), 111, 121, 131, 141 and 112, 122, 132, and 142 are memories (MEM), 113, 123, 133, and 143 are adders, and 150 is a calculation circuit. The MIC 110, the memories (MEM) 111, 112 and the adder 113 constitute a running average calculation circuit (RACC). Similarly, each block of the MIC 120 and the memories 121, 122, the MIC 130 and the memories 131, 132, and the MIC 140 and the memories 141, 142, constitutes the running average calculation circuit. The basic operation of this analyzer is explained with reference to FIGS. 2 and 3A to 3E.

In FIG. 2, the MIC 110 outputs an integration value $I_0$ obtained by multiplying the analysis selection signal $W(t)$ by the time signal t. When the switches 101 and 102 are located as shown in the drawing (solid line), the integration value $I_0$ is stored in the memories 4 and 5 in response to a write/read control signal (W/R). In this case, the time signal t is used as an address signal for storing the integration value $I_0$. Similarly, an integration value $I_1$ is obtained by multiplying the signal $W(t)$ by a square signal $t^2$ of the time signal t in the MIC 120, and the integration value $I_1$ is stored in the memories 6 and 7; an integration value $I_2$ is obtained by multiplying the signal $W(t)$ by a product signal $y(t) \cdot t$ of the time-series signal $y(t)$ and the time signal t in the MIC 130, and the integration value $I_2$ is stored in the memories 8 and 9; and an integration value $I_3$ is obtained by multiplying the signal $w(t)$ by the time-series signal $y(t)$ in the MIC 140, and the integration value $I_3$ is stored in the memories 10 and 11.

Figures 3A, 3B, 3C:
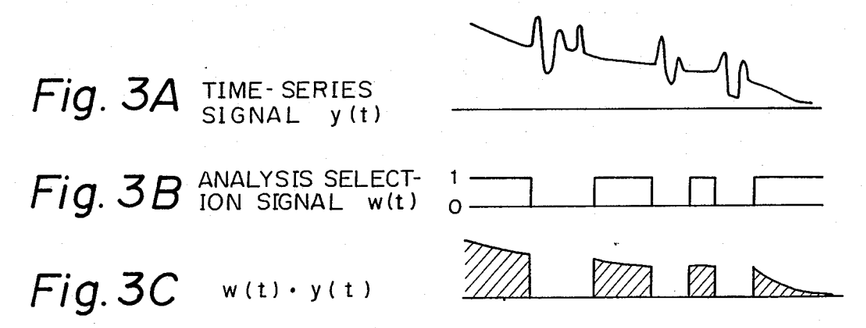
FIGS. 3A to 3E are views for explaining a method of analysis of the present invention.
Figure 3D:
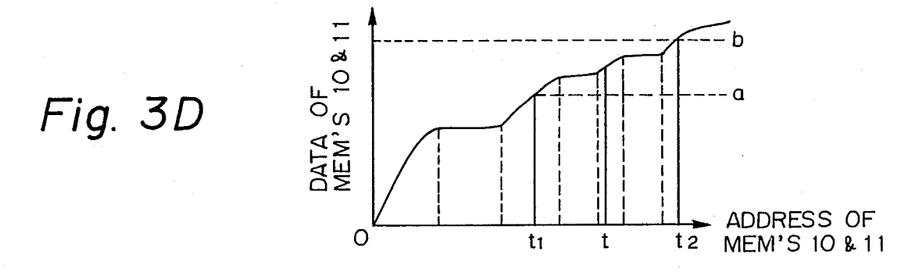

In FIGS. 3A to 3E, one example of the time-series signal $y(t)$ is shown in FIG. 3A, and the analysis selection signal $w(t)$ is shown in FIG. 3B. The product signal $w(t) \cdot y(t)$ of the signal $w(t)$ and the signal $y(t)$ (i.e., integration value $I_3$) is shown in FIG. 3C. The product signal $w(t) \cdot y(t)$ is obtained from the MIC 140. FIG. 3D represents data stored in the memories 10 and 11. In FIG. 3D, the ordinate shows the data, and the abscissa shows the address. The integration value $I_3$ is stored in the memories 10 and 11 by ring the time signal t as the address.

The switches 101 and 102 are located at opposite sides $t_1$ and $t_2$ (dotted line) after the above operations are finished. the analysis interval calculation circuit 100 outputs the start point $t_1$ and the end point $t_2$ of the analysis interval to all memories 4 to 11. In the drawing, the start point $t_1$ is shown by a signal A and the end point $t_2$ is shown by a signal B. Each memory outputs a first integration value between the time "0" and the time "$t_1$", and a second integration value between the time "0" and the time "$t_2$". In FIG. 3D, the outputs a and b show the data read from the memories 10 and 11 at the start point $t_1$ and the end point $t_2$.

Figure 3E:
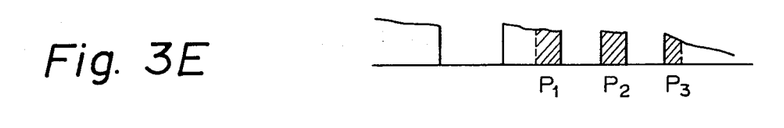

The difference between the first and the second integration values is calculated by the adders 113, 123, 133 and 143. For example, a difference value $x_1$ is obtained by the adder 113. That is, the adder 113 calculated the difference in the data of the memory 4 and the memory 5. Accordingly, the difference value $x_1$ means the integration value between the start point $t_1$ and the end point $t_2$. The value $x_4$ from the adder 143 is shown in FIG. 3E. The difference value $x_4$ means the integration value between the start point $t_1$ and the end point $t_2$, and is equivalent to a sum of the slant-lined areas $P_1$, $P_2$, and $P_3$. The integration values $x_1$ to $x_4$ are input to the calculation circuit 150. The calculation circuit 150 comprises a plurality of adders and multipliers, and obtains a slope of a regression curve of the echo signal based on a least square method. The values $x_1$ to $x_4$ are explained in detail in FIG. 9.

Figure 4:
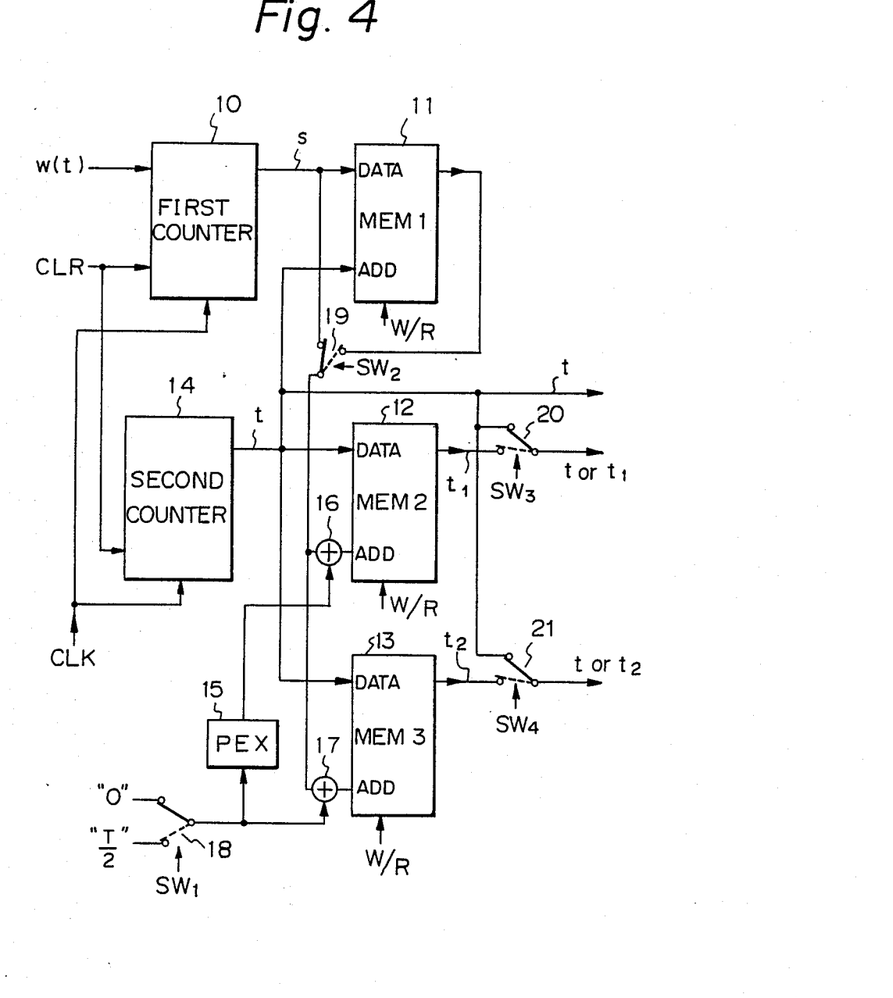
FIG. 4 is a detailed block diagram of an analysis interval calculation circuit shown in FIG. 2.

FIG. 4 shows a detailed block diagram of the analysis interval calculation circuit 100 shown in FIG. 2. In FIG. 4, reference number 10 denotes a first counter circuit, 11 to 13 memories (MEM), 14 a second counter circuit, 15 a polarity exchanger circuit, 16 and 17 adders, and 18 to 21 switches.

In a write mode, the switches 18 to 21 are located at the positions shown in the drawing (solid lines). The analysis selection signal $w(t)$ is input to an enable terminal of the first counter 10, and when the signal $w(t)$ is high ("1"), the first counter 10 counts (integrates) a clock signal CLK, and the second counter 14 sequentially counts the clock signal CLK and outputs the time signal t. The write operation to each memory 11 to 13 is performed in response to the write/read control signal W/R. An integration signal S is input in parallel to the memories 11 to 13. In this case, the memory 1 receives the integration signal S as the data (DATA), and the memories 12 and 13 receive the integration signal S as the address signal (ADD) through the adders 16 and 17. Further, the memory 11 receives the time signal t as the address signal, and the memories 12 and 13 receive the time signal t as the data.

Figure 5:
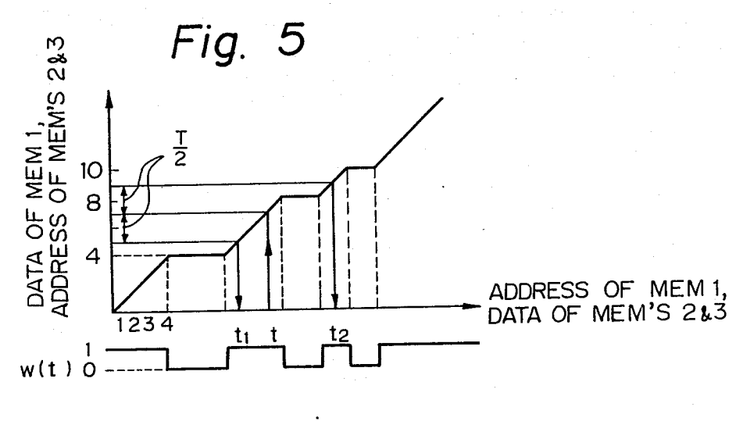
FIG. 5 represents data stored in memory.

FIG. 5 represents data stored in the memories 11 to 13. In FIG. 5, the ordinate denotes the data of the memory 11 or the address of the memories 12 and 13, and the abscissa denotes the address of the memory 11 or the data of the memories 12 and 13. As explained above, in the write mode, the memory 11 stores the output signal S as the data in accordance with the address denoted by the time signal t, and the memories 2 and 3 store the time signal t as the data in accordance with the address of the output signal S.

In a read mode, the switches 18 to 21 are located at the positions shown by dotted lines in FIG. 4. The start point $t_1$ and the end point $t_2$ are obtained in this mode. That is, when the write/read control signal W/R is input to each memory 11 to 13, the data stored in the memory 11 is output to the memories 12 and 13 as the address signal through the switch 19 and the adders 16, 17. The data stored in memories 12 and 13 are output in accordance with the address from the memory 11. In FIG. 5, the time data corresponding to the time interval T/2 is input to the adder 17 through the switch 18, the adder 17 adds the address at the time t to the address corresponding to the time interval T/2, and the memory 13 is accessed by the address obtained by the output of the adder 17. The memory 13 outputs the data indicating the end point $t_2$ as shown in FIG. 5. Similarly, the time data corresponding to the time interval T/2 is input to the adder 16 through the switch 18 and the polarity exchanger circuit 15. The adder 16 subtracts the address corresponding to the time interval T/2 from the address at the time t, and the memory 12 outputs the data indicating the start point $t_1$, as shown in FIG. 5.

Figure 6:
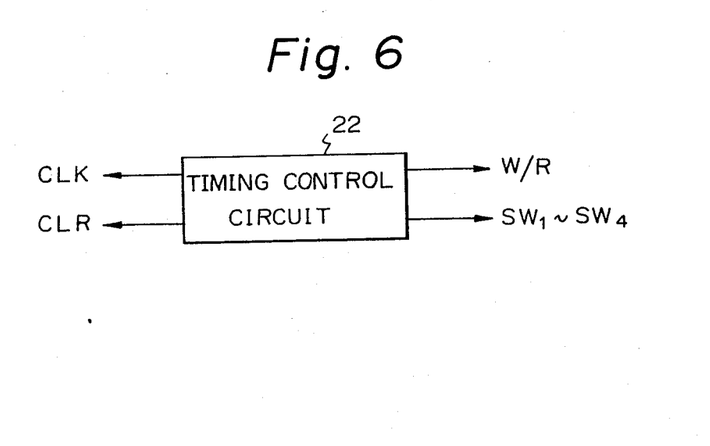
FIG. 6 is a block diagram of a timing control circuit for generating various control signals in FIG. 2.
Figure 9:
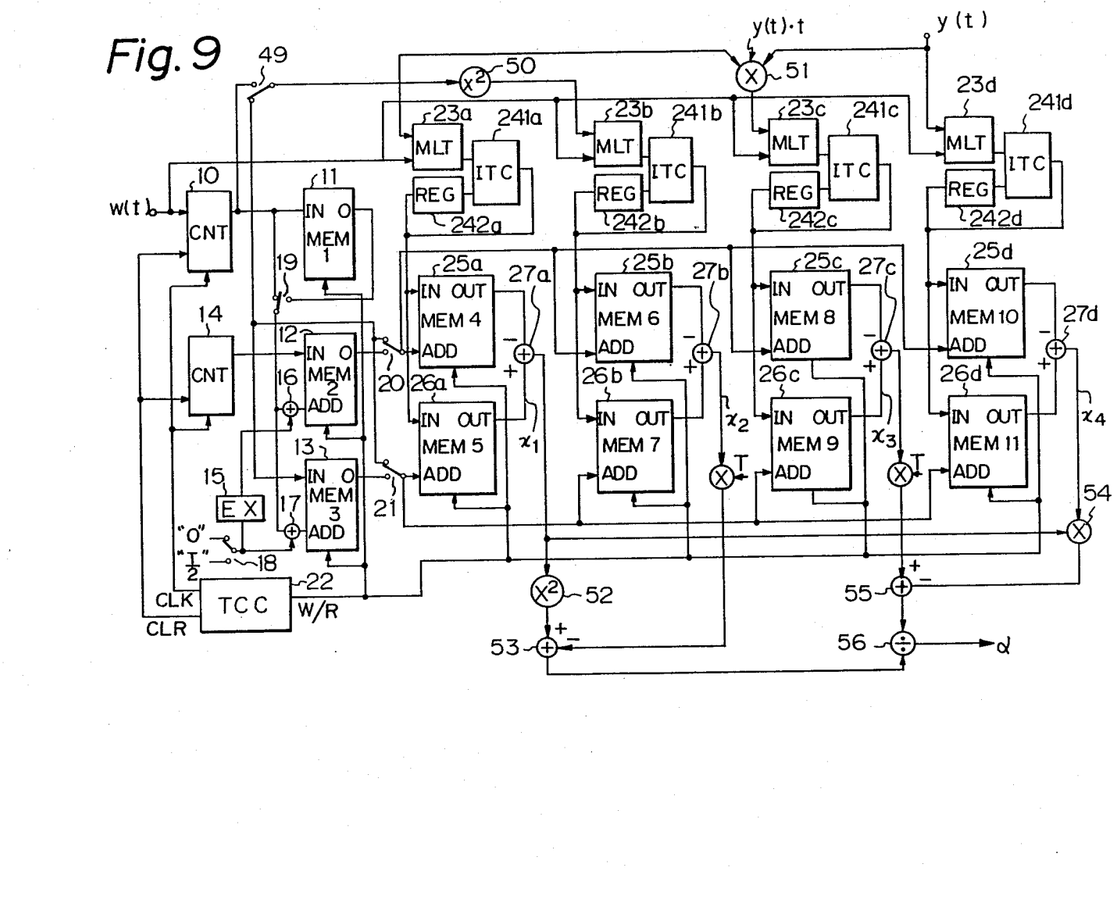
FIG. 9 is a detailed block diagram of the ultrasonic analyzer shown in FIG. 2.

FIG. 6 is a block diagram of a timing control circuit. The timing control circuit 22 generates switch signals $SW_1$ to $SW_4$ for switching the contact points of the switches 18 to 21 in accordance with the write or read mode, the clear signal CLR for resetting the first counter 10 and the second counter 14, the clock signal CLK, and the write/read control signal W/R for controlling the write or read mode. The connection of timing control circuit 22 within a system is shown in FIG. 9.

Figure 7:
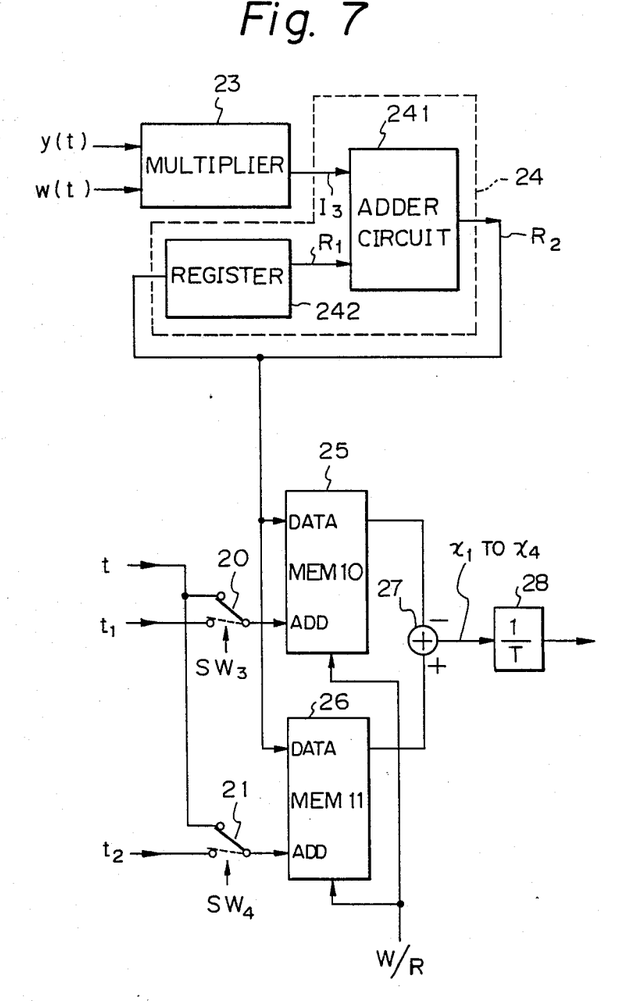
FIG. 7 is a detailed block diagram of a running average calculation circuit shown in FIG. 2.

FIG. 7 is a detailed block diagram of the running average circuit shown in FIG. 2. In FIG. 7, reference number 23 denotes a multiplication circuit for multiplying the time-series signal y(t) by the analysis selection signal w(t), 24 is an integration circuit comprising of an adder circuit 241 and a register 242, 25 and 26 are memories (MEM), 27 is an adder, and 28 is a divider circuit. The multiplication circuit 23 and the integration circuit 24 correspond to the multiplication integration circuit (MIC) 140 in FIG. 2, and the memories 25 and 26 correspond to the memories 10 and 11 in FIG. 2.

The integration value $I_3$ is obtained by multiplying the time-series signal y(t) by the analysis selection signal w(t) in the multiplication circuit 23. These signals are shown in FIGS. 3A to 3C. The register 242 stores the data from the adder. The adder circuit 241 adds the integration value $I_3$ to the previous data $R_1$, and the resultant data $R_2$ is fed back to the register 242 and output to the memories 25 and 26. In the write mode, the resultant data $R_2$ is stored in the memories 25 and 26 in accordance with the address of the time signal t transferred from the counter 14 through the switches 20 and 21. Therefore, the memories 25 and 26 store the data represented by the table shown in FIG. 3D.

In the read mode, the switches 20 and 21 are switched to the position shown by a dotted line. The start point $t_1$ and the end point $t_2$ are output from the analysis interval calculation circuit 100 shown in FIG. 4, and input to these memories as the address, and the data stored in these memories are output to the adder 27. The adder 27 calculates the difference between the data b at the time $t_2$ and the data a at the time $t_1$ as shown in FIG. 3D. The resultant data from the adder 27 is shown by $P_1$, $P_2$, and $P_3$ in FIG. 3E. The divider circuit 28 calculates the running average value. The running average value can be obtained by dividing the integration value (difference value) b-a by the analysis interval T. the analysis interval also denotes the number of the sampling data in the analysis interval T.

Figure 8:
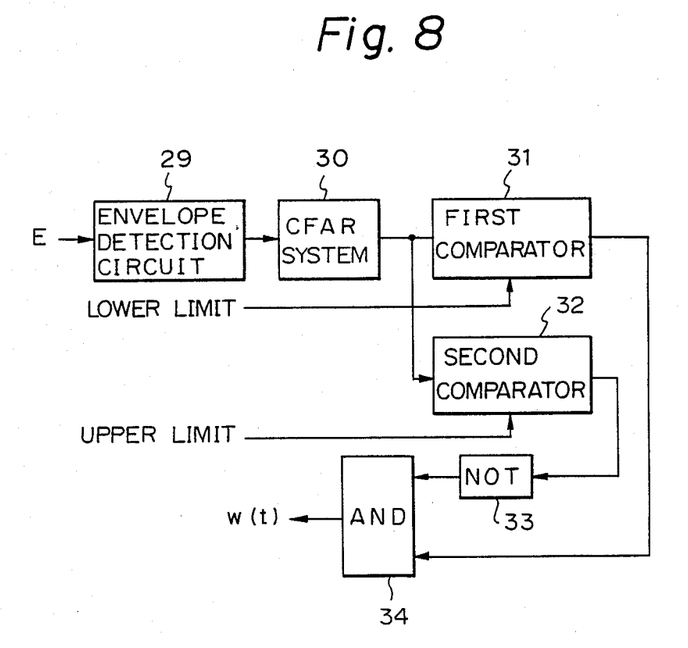
FIG. 8 is a schematic block diagram of an analysis selection signal generation circuit according to an embodiment of the present invention.

FIG. 8 is a schematic block diagram of an analysis selection signal generation circuit according to the present invention.

In FIG. 8, reference number 29 denotes an envelope detection detect, 30 is a CFAR system (described below), 31 and 32 are comparators, 33 is a NOT circuit, and 34 is an AND circuit. "E" denotes the echo signal reflected from the living body when the ultrasonic pulse is irradiated thereto. The echo signal E contains the various noises $N_1$ to $N_6$ as shown in FIG. 1B. The envelope detection circuit 29 detects the envelope of the echo signal E and obtains a logarithm curve thereof. The CFAR system 30 applies a system employed in a radar system: "CFAR" means Constant False Alarm Rate. In general, the CFAR system is used for discriminating an unclear image contained in a reflected signal, and therefore, the present invention utilizes the CFAR technique for detecting the various noises contained in the echo signal E. The CFAR system 30 generates a CFAR signal based on the logarithm curve of the envelope. The CFAR signal contains various noises, and therefore, the first comparator 31 cuts large dip noises exceeding a lower limit level, and the second comparator 32 cuts large peak noises exceeding an upper limit level. The output of the comparator 32 is inverted by the NOT circuit 33, and therefore, the analysis selection signal w(t) can be obtained from the AND circuit 34. That is, when the CFAR signal exceeds these limit lines, the analysis selection signal w(t) becomes low level ("0"), and when the CFAR signal is between the upper limit and the lower limit, the analysis selection signal w(t) becomes high level ("1"). The waveform of the signal w(t) is shown in FIG. 3B.

The feature of the analysis selection signal generation circuit lies in the utilization of the CFAR system as explained above. A conventional analysis selection signal generation circuit does not utilize the CFAR system.

FIG. 9 is a detailed block diagram of the ultrasonic analyzer shown in FIG. 2.

In FIG. 9, 23a to 23d denote multiplication circuits (MLT), 241a to 241d are integration circuits (ITC), 242a to 242d are register (REG), 25a to 25d and 26a to 26d are memories (MEM), 27a to 27d are adders, 10 and 14 are counters, 11 to 13 are memories (MEM), 15 is a polarity exchanger circuit (EX), 22 is a timing control circuit (TCC), 16, 17 and 53, 55 are adders, 18 to 21 and 49 and switches, 50 and 52 are square circuits, 51 and 54 are multiplication circuits, and 56 is a divider circuit.

The multiplication circuit 23a, the integration circuit 241a, and the register 242a correspond to the multiplication integration circuit 110 shown in FIG. 2, and the memories 25a and 26a correspond to the memories 111 and 112 shown in FIG. 2. Similarly, the other multiplication integration circuits and memories correspond to units shown in FIG. 2. Further, the counters 10 and 14, the memories 10 to 13, the polarity exchanger circuit 15, and the timing control circuit 22 correspond to the analysis interval calculation circuit 100 shown in FIG. 2. Still further, the square circuits 52, the adders 53 and 55, the multiplier 54, and the divider circuit 56 correspond to the calculation circuit 150 in FIG. 2.

The object of the present invention is to obtain a slope $\alpha$ of the regression curve of the echo signal by using the least square method. The attentuation coefficient is one of the acoustic characteristics contained in the echo signal, as explained above, and in general, it is possible to clarify an inner condition of the living body by checking the slope of the echo signal. Therefore, it is necessary to obtain a more precise slope for correctly checking the living body. To achieve the above object, it is necessary to eliminate or avoid the various noises contained in the echo signal.

The ultrasonic analyzer shown in FIG. 9 can obtain a specific function f(t) based on the analysis selection signal w(t) and the time-series signal y(t). The specific function f(t) having n-order is given as follows.

$$f(t) = a_n t^n + a_{n-1} t^{n-1} + \ldots + a_1 t + a_0 \tag{1}$$

The factors $a_n$, $a_{n-1}$ ... $a_1$, $a_0$ denote the slope $\alpha$ and are output from the calculation circuit 150 (FIG. 2).

When the frequency spectrum of the echo signal has a gaussian distribution, the primary function is suitable for the specific function as the regression curve.

To simplify the explanation, the specific function f(t) is given as follows.

$$f(t) = a_1 t + a_0 \tag{2}$$

As is obvious, the formula (2) denotes a linear function and the factor $a_1$ denotes the slope $\alpha$.

The factors $a_1$ and $a_0$ can be obtained by the known linear regression method, as follows.

$$a_1 = \frac{T\Sigma w(t)y(t)t - \Sigma w(t)y(t) \cdot \Sigma w(t)t}{T\Sigma w(t)t^2 - (\Sigma w(t)t)^2} \quad (3)$$

$$a_0 = \frac{\Sigma w(t)y(t) \cdot \Sigma w(t)t - \Sigma w(t)y(t)t \cdot \Sigma w(t)t}{T\Sigma w(t)t^2 - (\Sigma w(t)t)^2} \quad (4)$$

The value "$T\Sigma w(t)t$" can be obtained from the adder 27a, the value "$T\Sigma w(t)t^2$" from the adder 27b, the value "$T\Sigma w(t)y(t)t$" from the adder 27c, and the value "$T\Sigma w(t)y(t)$" from the adder 27d.

The square circuit 52 calculates the value $(\Sigma w(t)t^2)^2$, the adder 53 calculates the value $(\Sigma w(t)t^2)^2 - \Sigma w(t)t^2$, and the multiplier 54 calculates the value $(\Sigma w(t)t)(\Sigma w(t)y(t))$. Accordingly, the divider circuit 56 calculates the formula (1) and can obtain the factor $a_1$ as the slope $\alpha$.

In the case, the square circuit 50 calculates the value "$t^2$" based on the time signal t from the second counter 14. The multiplication circuit 51 calculates the value "$y(t)t$" based on the time signal t an the time-series signal.

Figure 10:
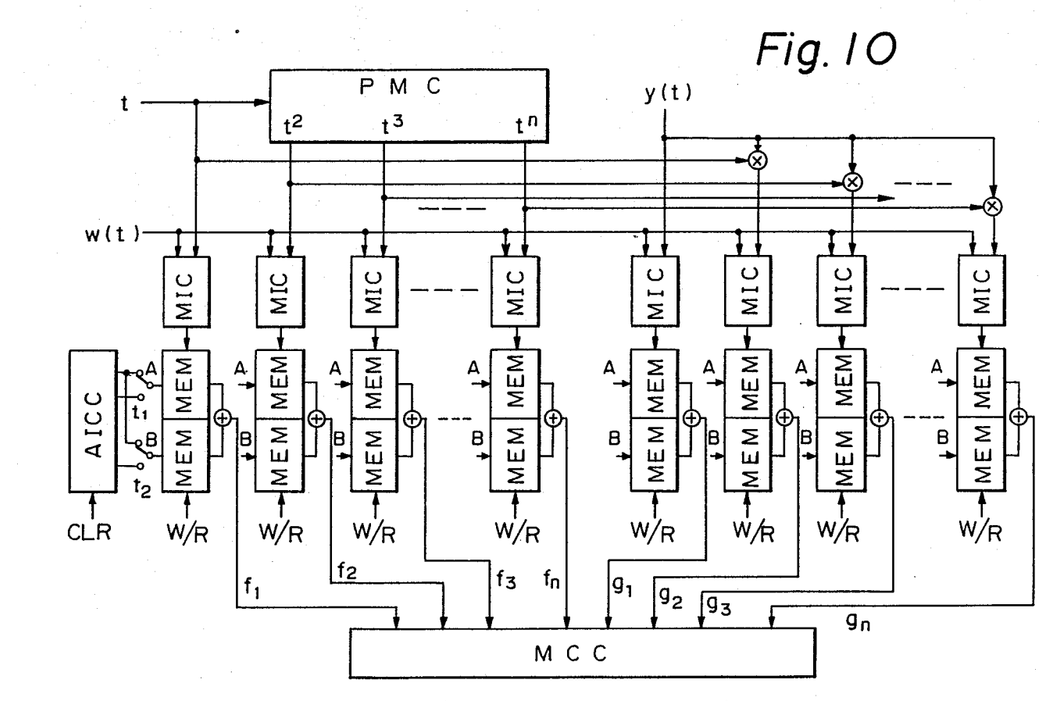
FIG. 10 is a schematic block diagram of an ultrasonic analyzer according to another embodiment of the present invention.

FIG. 10 is a schematic block diagram of the ultrasonic analyzer according according to another embodiment and shown for the case of the primary function as the specific function (see, formula (2)), this embodiment is in case of n-order function as the specific function.

In FIG. 10, PMC denotes a power multiplication circuit for outputting power signals ($t^2, t^3 \ldots t^n$) of the time signal t. Each of these powers signals is input to the corresponding multiplication integration circuit (MIC). Each product of the time-series signal y(t) and the power signal ($t^2, t^3 \ldots t^n$) is input to the corresponding multiplication integration circuit. While, the analysis selection signal w(t) is input in parallel to all MIC's. MCC denotes a matrix calculation circuit for calculating the following matrix.

That is, from the formula (1), a sum of the regression square error ER is given as follows.

$$ER = \sum_{i=0}^{m-1} w_i [y_i - (\text{formula (1)})]^2 \quad (5)$$

Where, "$y_i$" is an input signal as a discrete time signal at the time $t_i$. That is, the value of the input signal ($y_0$, $y_1, y_2 \ldots$) denotes the value corresponding to the time ($t_0, t_1, t_3 \ldots$).

The factors ($a_n, a_{n-1}, \ldots, a_0$) are determined from the minimum value of the regression square error ER.

For obtaining the minimum value, the following formula is given.

$$\frac{\partial ER}{\partial a_p} = 0 \quad (p = 0, 1, \ldots, n) \quad (6)$$

The formula (6) is given by the following matrix.

$$\begin{pmatrix} \sum_t w(t)t^{2n} & \sum_t w(t)t^{2n-1} & \ldots & \sum_t w(t)t^{n+1} & \sum_t w(t)t^n \\ \sum_t w(t)t^{2n-1} & \sum_t w(t)t^{2n-2} & \ldots & \sum_t w(t)t^n & \sum_t w(t)t^{n-1} \\ \vdots & \vdots & & \vdots & \vdots \\ \sum_t w(t)t^{n+2} & \sum_t w(t)t^{n+1} & \ldots & \sum_t w(t)t^3 & \sum_t w(t)t^2 \\ \sum_t w(t)t^{n+1} & \sum_t w(t)t^n & \ldots & \sum_t w(t)t^2 & \sum_t w(t)t \\ \sum_t w(t)t^n & \sum_t w(t)t^{n-1} & \ldots & \sum_t w(t)t & \sum_t w(t) \end{pmatrix} \begin{pmatrix} a_n \\ a_{n-1} \\ \vdots \\ a_2 \\ a_1 \\ a_0 \end{pmatrix} = \begin{pmatrix} \sum_t w(t)y(t)t^n \\ \sum_t w(t)y(t)t^{n-1} \\ \vdots \\ \sum_t w(t)y(t)t^2 \\ \sum_t w(t)y(t)t \\ \sum_t w(t)y(t) \end{pmatrix}$$

The factors ($a_n, a_{n-1}, \ldots, a_0$) can be obtained by solving the above matrix. Therefore, in case of n-order function, it i necessary to obtain the integration value of the formula $w(t)y(t)t^k$ and $w(t)t^k$ (k = O to n) for obtaining the above factors. The slope $\alpha$ of the n-order function can be obtained by differentiating the n-order function in the matrix calculation circuit.

Each integration value in FIG. 10 is given as follows.
$f_1 = \Sigma w(t)t$, $f_2 = \Sigma w(t)t^2$, $f_3 = \Sigma w(t)t^3$, $f_n = \Sigma w(t)t^n$,
$g_1 = \Sigma w(t)y(t)$, $g_2 = \Sigma w(t)y(t)t$, $g_3 = \Sigma w(t)y(t)t^2$,
$g_n = \Sigma w(t)y(t)t^n$. In the above calculation, the analysis interval T is included in each calculation.

We claim:

1. An ultrasonic analyzer used in an ultrasonic diagnosis instrument capable of launching signals into and receiving time-series signals reflected from a media, comprising:
   analysis means for receiving a time signal and an analysis selection signal;
   first means for determining a start point and an end point of an analysis interval, to be analyzed based on the analysis selection signal and the time signal, of the time-series signal;
   second means for generating a plurality of integration values based on multiplication signals, including means for providing said multiplication signals by multiplying said analysis selection signal by at least one of said time signal, a square of said time signal, a product of said time signal an said time-series signal, and said time-series signal;
   third means for storing each of said integration values in accordance with said time signal; and
   fourth means for calculating a slope of a regression curve, including means for determining differences between said integration values based on said start point and said end point, and said slope being based on said differences.

2. An ultrasonic analyzer as claimed in claim 1, wherein said first means comprises:
  first counter means for receiving and counting a clock signal in response to said analysis selection signal, and for outputting an integration signal in response to said clock signal,
  second counter means for counting said clock signal, and for outputting said time signal;
  first memory means for storing said integration signal in accordance with said time signal;
  second and third memory means for storing said time signal in accordance with said integration signal; and
  first and second adder means for providing first and a second address by adding another address corresponding to a half of said analysis interval to said integration signal; wherein
  said second memory means outputs said start point based on said first address from said first adder means, and said third memory means outputs said end point based on said second address from said second adder means.

3. An ultrasonic analyzer as claimed in claim 2, further comprising:
  timing control means for generating said clock signal; and
  clear means for resetting said first and second counter means.

4. An ultrasonic analyzer as claimed in claim 2, wherein each of said first, second and third memory means comprises:
  table means for storing said integration signal and said time signal, said table means being selectively addressed by one of said integration signal and said time signal, and storing the remaining one of said integration signal and said time signal.

5. An ultrasonic analyzer as claimed in claim 2, and further comprising, a timing control circuit for generating said clock signal; a write/read control signal for switching between a write mode and read mode, said write/read control signal being input in parallel to said third means; and a clear signal for resetting said first and second counter means.

6. An ultrasonic analyzer as claimed in claim 1, wherein said second means comprises:
  multiplication means for multiplying said analysis selection signal by said time-series signal and outputting a multiplication value;
  adder means for integrating said multiplication value and outputting said integration values responsive to said integration; and
  register means for temporarily storing said integration value.

7. An ultrasonic analyzer as claimed in claim 6, wherein said third means comprises:
  first and second memory means for storing said integration values from said adder means in accordance with said time signal, said first and second memory means outputting said stored values in accordance with said start and end points;
  additional adder means for calculating a difference value of data stored in said first and second memory mean in accordance with said start and end points; and
  divider means for calculating a running average value by dividing said difference value by a value corresponding to said analysis interval.

8. An ultrasonic analyzer as claimed in claim 7, wherein each of said first and second memory means comprises:
  table means for storing said integration values.

9. An ultrasonic analyzer as claimed in claim 7, and further comprising, a timing control circuit for generating said clock signal; a write/read control signal for switching between a write mode and read mode, said write/read control signal being input in parallel to said third means.

10. An ultrasonic analyzer as claimed in claim 6, wherein said third means comprises: first and second memories for storing said integration value from said adder circuit as data in the write mode when said time signal in input as the address through a plurality of switches, said first and second memories outputting stored data in the read mode when said start and end points are input as the address through each of said switches; an adder circuit for calculating a difference value of data at said start a and end points between said first and second memories in the read mode; and a divider circuit for calculating a running average value by dividing said difference value by said analysis interval.

11. An ultrasonic analyzer as claimed in claim 6, and further comprising, a timing control circuit for generating said clock signal; a write/read control signal for switching between a write mode and read mode, said write/read control signal being input in parallel to said third means.

12. An ultrasonic analyzer as claimed in claim 1, wherein said forth means further comprises:
  square means for calculating a square value of a first one of said differences;
  multiplication means for multiplying said first one of said differences by a second one of said differences;
  first adder means for adding an output of said square means to a third one of said differences;
  second adder means for adding an output of said multiplication means to a fourth one of said differences; and
  divider means for calculating said slope of said regression curve by dividing an output of said second adder means by an output of said first adder means.

13. An ultrasonic analyzer as claimed in claim 12, and further comprising, a timing control circuit for generating said clock signal; a write/read control signal for switching between a write mode and read mode, said write/read control signal being input in parallel to said third means.

14. An ultrasonic analyzer as claimed in claim 1, further comprising:
  square means for generating said square of said time signal; and wherein said means for providing includes
  multiplication means for generating said product of said time signal and said time-series signal.

15. An ultrasonic analyzer as claimed in claim 14, and further comprising, a timing control circuit for generating said clock signal; a write/read control signal for switching between a write mode and read mode, said write/read control signal being input in parallel to said third means.

16. An ultrasonic analyzer as claimed in claim 1, further comprising means for generating said analysis selection signal including:
  envelope detection means for obtaining an envelope of said time-series signal, and for obtaining a signal having a logarithm characteristic from said envelope;

constant false alarm rate (CFAR) system means for generating a CFAR signal based on said logarithm signal;

first comparator means for comparing said CFAR signal with a lower limit level;

second comparator means for comparing said CFAR signal with an upper limit level;

logic NOT means for inverting an output of said second comparator means; and logic AND means for generating said analysis selection signal based on a logical AND of an output of said logic NOT means and an output of said first comparator means.

17. An ultrasonic analyzer used in an ultrasonic diagnosis instrument capable of launching signals into and receiving time-series signals reflected from a media, comprising:

analysis means for receiving a time signal and an analysis selection signal;

first means for determining a start point and an end point of an analysis interval, to be analyzed based on the analysis selection signal and the time signal, of the time-series signal;

second means for generating various integration values based on various multiplication signals, including means for calculating said multiplication signals by multiplying said analysis selection signal by at least one of said time signal, a power of said time signal, a product of said power and said time-series signal, and said time series signal;

third means for storing each of said integration values in accordance with said time signal;

fourth means for calculating a slope of a regression curve including means for performing calculations with a matrix of said integration values; and fifth means for providing said power signal of said time signal.

* * * * *